United States Patent
Carnes et al.

(10) Patent No.: US 9,218,671 B2
(45) Date of Patent: Dec. 22, 2015

(54) TIME ALIGNMENT DISPLAY TECHNIQUE FOR A MEDICAL DEVICE

(71) Applicant: Covidien LP, Mansfield, MA (US)

(72) Inventors: Tony C. Carnes, Gainesville, FL (US); Henry Szymanski, Boulder, CO (US); Kevin R. Birkett, Newberry, FL (US)

(73) Assignee: Covidien LP, Boulder, CO (US)

( * ) Notice: Subject to any disclaimer, the term of this patent is extended or adjusted under 35 U.S.C. 154(b) by 204 days.

(21) Appl. No.: 13/778,382

(22) Filed: Feb. 27, 2013

(65) Prior Publication Data

US 2014/0022256 A1    Jan. 23, 2014

Related U.S. Application Data

(60) Provisional application No. 61/672,582, filed on Jul. 17, 2012.

(51) Int. Cl.

| A61B 5/024 | (2006.01) |
|---|---|
| A61B 5/08 | (2006.01) |
| A61B 5/1455 | (2006.01) |
| A61B 5/0205 | (2006.01) |
| A61B 5/021 | (2006.01) |
| G06T 11/20 | (2006.01) |
| G06T 11/00 | (2006.01) |

(52) U.S. Cl.
CPC .............. *G06T 11/00* (2013.01); *A61B 5/02416* (2013.01); *A61B 5/14553* (2013.01); *G06T 11/206* (2013.01); *A61B 5/021* (2013.01); *A61B 5/024* (2013.01); *A61B 5/02055* (2013.01); *A61B 5/0816* (2013.01)

(58) Field of Classification Search
None
See application file for complete search history.

(56) References Cited

U.S. PATENT DOCUMENTS

| 7,062,251 | B2 | 6/2006 | Birkett et al. | |
|---|---|---|---|---|
| 8,002,707 | B2 | 8/2011 | Ooshima | |
| 8,294,716 | B2 | 10/2012 | Lord et al. | |
| 2009/0054743 | A1* | 2/2009 | Stewart | 600/301 |
| 2010/0261977 | A1* | 10/2010 | Seely | 600/300 |
| 2011/0004071 | A1* | 1/2011 | Faiola | A61B 5/7445 600/300 |
| 2013/0052621 | A1* | 2/2013 | el Kaliouby et al. | 434/236 |

* cited by examiner

*Primary Examiner* — Maurice L McDowell, Jr.
*Assistant Examiner* — Donna J Ricks
(74) *Attorney, Agent, or Firm* — Carter, DeLuca, Farrell & Schmidt, LLP

(57) ABSTRACT

A system is presented including at least one sensor and a monitor in operable communication with the at least one sensor. The monitor is configured to display a plurality of graphs each representing a measured physiologic parameter versus time, the plurality of graphs configured to be aligned with respect to each other along a time axis. A marker moves along the time axis of each of the plurality of graphs in response to an input received from an input unit. The plurality of graphs are stacked with respect to each other in a vertical orientation and in a non-overlapping manner.

18 Claims, 10 Drawing Sheets

TIME ALIGNMENT DISPLAY TECHNIQUE FOR A MEDICAL DEVICE

CROSS REFERENCE TO RELATED APPLICATION

The present application claims the benefit of and priority to U.S. Provisional Application Ser. No. 61/672,582, filed on Jul. 17, 2012, the entire contents of which are incorporated herein by reference.

TECHNICAL FIELD

The present disclosure relates to medical devices and, more particularly, to systems and methods for medical devices that display patient-related data.

BACKGROUND

A wide variety of devices have been developed for non-invasively monitoring physiologic characteristics of patients. For example, an oximetry sensor system may non-invasively detect various patient blood flow characteristics, such as blood-oxygen saturation of hemoglobin in blood, volume of individual blood pulsations supplied to tissue, and/or the rate of blood pulsations corresponding to each heart beat of a patient. During operation, the oximeter sensor emits light and photo-electrically senses the absorption and/or scattering of the light after passage through perfused tissue. A photo-plethysmographic waveform, which corresponds to cyclic attenuation of optical energy through the patient's tissue, may be generated from the detected light. Additionally, one or more physiologic characteristics may be calculated based upon an amount of light absorbed or scattered. More specifically, the light passed through tissue may be selected to be of one or more wavelengths that may be absorbed and/or scattered by the blood in an amount correlative to the amount of the blood constituent present in the blood. The amount of light absorbed and/or scattered may then be used to estimate the amount of blood constituent in tissue using various algorithms.

The automated capture of sensed physiologic values from one or multiple medical devices may lead to improved patient care. However, the act of capturing and displaying the data/information from medical sensors does not necessarily improve care. What may improve care is the ability to present the captured data/information in new ways and to identify cause and effect relationships for such captured data/information.

SUMMARY

The present disclosure relates to systems and methods that generally include at least one sensor and a monitor in operable communication with the at least one sensor. The systems and methods allow the monitor to be configured to display a plurality of graphs each representing a measured physiologic parameter versus time, the plurality of graphs configured to be aligned with respect to each other along a time axis. A marker moves along the time axis of each of the plurality of graphs in response to an input received from an input unit.

The aspects and features of the present disclosure are advantageous in that they provide a marker that is a time scroll bar. The aspects and features of the present disclosure are advantageous in that they allow a graph of each measured physiologic parameter to be indicative of a trend of the measured physiologic parameter over a period of time. The aspects and features of the present disclosure are advantageous in that they allow the plurality of graphs to be stacked with respect to each other in a vertical orientation and in a non-overlapping manner. The aspects and features of the present disclosure are advantageous in that they allow the marker to be a vertical time scroll bar configured to intersect the plurality of graphs at a common point on the time axis.

The aspects and features of the present disclosure are advantageous in that they allow the marker to be moved to a previous measured time period or point in time corresponding to historical medical events of interest for evaluating the measured physiologic parameters during that measured time period or point in time. The aspects and features of the present disclosure are advantageous in that they provide, as the marker is moved across one graph of the plurality of graphs to a point in time, all the measured physiologic parameters of all of the plurality of graphs to be displayed on a monitor at that point in time and to be simultaneously analyzed. The aspects and features of the present disclosure are advantageous in that they provide the monitor with a storage module for storing values the measured physiologic parameters, where the values are periodically recorded during predefined points of time. The aspects and features of the present disclosure are advantageous in that they provide, by moving the marker across a graph of the plurality of graphs, a direct relationship to be established between all the physiologic parameters at any given point in time.

Certain embodiments of the present disclosure may include some, all, or none of the above advantages and/or one or more other advantages readily apparent to those skilled in the art from the drawings, descriptions, and claims included herein. Moreover, while specific advantages have been enumerated above, the various embodiments of the present disclosure may include all, some, or none of the enumerated advantages and/or other advantages not specifically enumerated above.

BRIEF DESCRIPTION OF THE DRAWINGS

The present disclosure and its various aspects and features are described hereinbelow with reference to the accompanying drawings, wherein.

Figure 1:
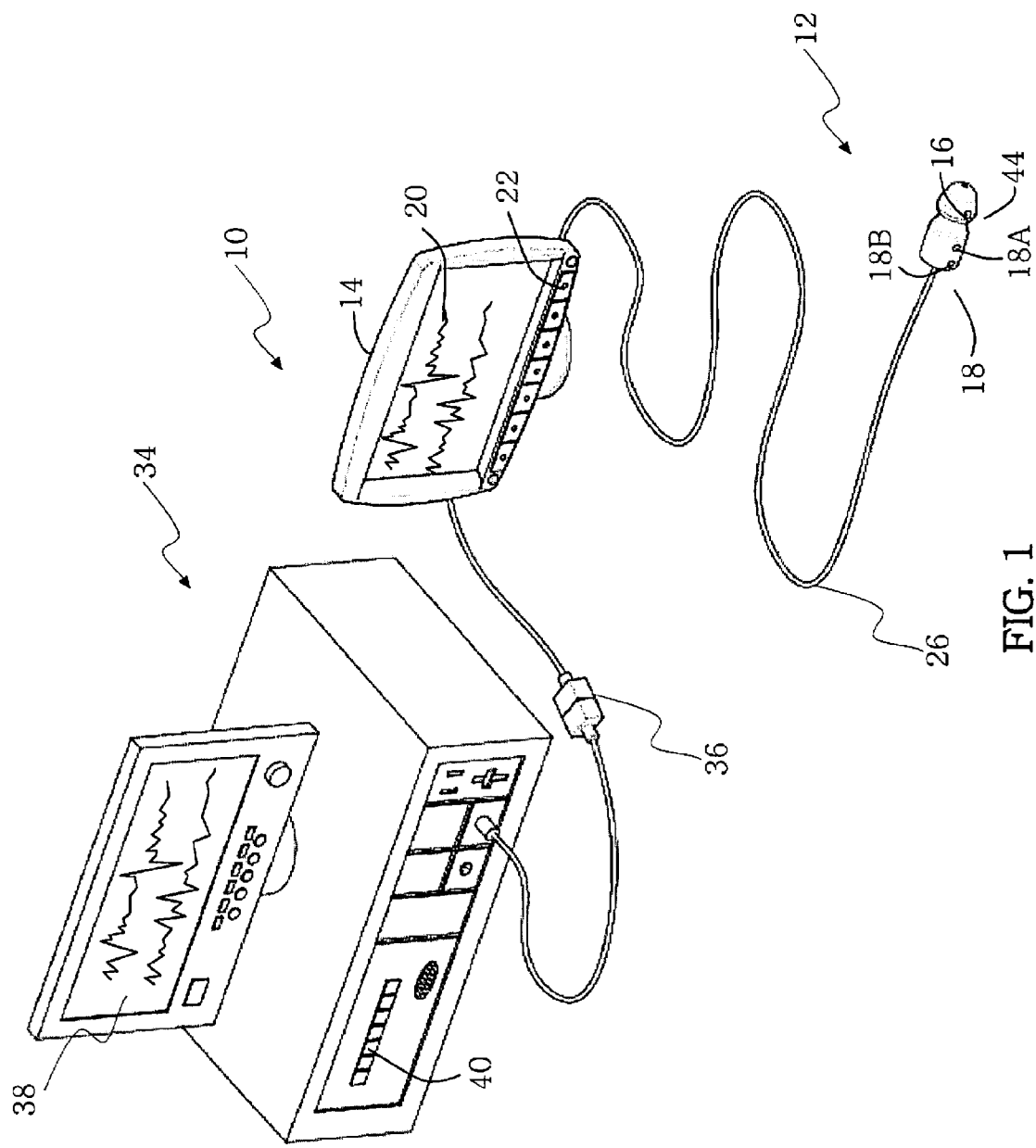
FIG. 1 is a perspective view of an illustrative embodiment of a monitoring system configured to be used with a sensor for regional saturation, in accordance with an aspect of the present disclosure.

The figures depict embodiments of the present disclosure for purposes of illustration only. One skilled in the art will readily recognize from the following disclosure that alternative embodiments of the structures and methods illustrated herein may be employed without departing from the principles of the present disclosure described herein.

DETAILED DESCRIPTION

Although the present disclosure will be described in terms of specific embodiments, it will be readily apparent to those skilled in this art that various modifications, rearrangements and substitutions may be made without departing from the spirit of the present disclosure. The scope of the present disclosure is defined by the claims appended hereto.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The term "clinician" refers to any medical professional (i.e., doctor, surgeon, nurse, or the like) performing and/or monitoring and/or supervising a medical procedure involving the use of exemplary embodiments described herein.

The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

In accordance with the exemplary embodiments of the present disclosure, one method that may be used to better visualize medical information acquired from medical devices is through the use of charts/graphs. In particular, with a trend chart, a clinician or medical professional may be in a better position to determine when, for example, a negative trend has commenced instead of merely identifying when a parameter related to patient data crossed a certain threshold. However, one disadvantage of using such trend graphs is that it is often difficult to determine exact values, especially exact values for the exact same moment in time when looking across multiple graphs/charts or multiple parameters on a single graph/chart. A commonly used method to determine a value at a spot on a graph/chart is to hover over the line at the desired point by using a mouse pointer. On touchscreen systems that do not utilize a mouse, there is no concept of a hover. Thus, in view of such deficiencies, the exemplary embodiments of the present disclosure describe a technique that achieves the same functionality, even across multiple stacked graphs, without using a mouse.

Patient data may include any patient identifiers, medical history, clinician notes, alarm thresholds, alarm events, device settings, measurements of values indicating physiologic conditions, such as oxygen saturation levels, pulse rates, heart rates, other vital signs, and any other data input to or output from medical devices. It is noted that monitored and/or measured physiologic parameters include at least one of: oxygen saturation, pulse rate, respiration rate, heart rate, temperature, arterial pressure, blood pressure, and hydration status. However, one skilled in the art may monitor any known physiologic parameters. Medical devices may be any devices that are used for monitoring, tracking and/or treating patients. For example, medical devices may include a ventilator connected to a patient to deliver respiration therapy, a pulse oximeter that monitors the oxygen saturation of a patient's blood, a device for tracking a patient within a hospital with or without monitoring a physiologic condition, as well as other medical devices known to those of skill in the art. Medical devices may include a component for identifying the particular medical device, including, but not limited to, radio frequency identification chips and unique bar codes.

Data and/or information from multiple medical devices may be captured and placed on one or more trend charts/graphs. In one exemplary embodiment, the technique involves placing the trend charts/graphs on a display that enables the charts/graphs to be stacked, in a vertical direction or orientation, such that the x-axis of the charts/graphs (i.e., the time axis) aligns across all the charts/graphs. In addition, the charts/graphs are placed on a display that includes a slider bar. For example, if the medical professional touches the slider bar, a vertical marker or line is generated, which crosses all charts/graphs at a location which corresponds to the same point in time.

At the point of intersection of the vertical line and all horizontal lines (x-axis or time axis) that represent physiologic values, the value at that common point is displayed. Therefore, the time value may be displayed once because it is the same across all horizontal lines on the charts/graphs and, may be displayed at the top or bottom of the display screen away from the other data points. As a result, a medical professional may extract data or information from any common point, on the time axis, across a plurality of different physiologic charts/graphs. This technique enables the medical professional to evaluate and/or analyze and/or scrutinize data or information at any point in time related to a plurality of different physiologic parameters via a single display panel.

Moreover, as the medical professional slides the vertical marker in a horizontal direction, the vertical marker horizontally moves across the charts/graphs and triggers the display of each value at the intersected point in time. The placement of the displayed set of values may be in tabular display, on the top, bottom, or side of the charts/graphs, or it may be in a smaller font adjacent to the intersection point. In one exemplary embodiment, if a tabular display is included with the chart/graph, using the up and down keys to scroll through the tabular display may cause the vertical marker to scroll across the graph/chart and display the values at the intersection points. These tabular displays may be stored or recorded in a storage module/unit.

The techniques of the present disclosure may be used in conjunction with any type of displayed medical data/information. For example, the medical data/information may be collected using a particular sensor or set of sensors, such as, but not limited to, regional oxygen saturation sensors. By way of example only, an INVOS® cerebral/somatic sensor, such as an OxyAlert™ NIR sensor by Somanetics or a SomaSensor® sensor by Somanetics, which may include one or more emitters and a pair of detectors for determining site-specific oxygen levels, may represent such sensors. In addition, when analyzing data via the INVOS® cerebral/somatic sensor or any other type of sensor, the present techniques allow a medical professional or user to highlight the area under the curve or plot for each channel. The present techniques may also be used in conjunction with other types of medical sensors, such as pulse oximetry sensors or carbon dioxide sensors. One skilled in the art may contemplate using a plurality of different sensors for measuring and/or monitoring a plurality of different physiologic parameters.

By way of example, the present techniques may be incorporated into systems that collect and display at least medical data. One non-limiting example includes systems incorporating a sensor capable of performing regional oximetry, and storing and providing any type of patient-related data, which are described below with respect to FIGS. 1 and 2. Of course one skilled in the art may contemplate using any type of sensors to measure any types of patient parameter data in the exemplary embodiments described with reference to FIGS. 1 and 2.

Referring to FIG. 1, a patient monitoring system 10 that may be used in conjunction with a medical sensor 12 is depicted. Although the depicted exemplary embodiments relate to sensors for use on a patient's head, it should be understood that, in certain embodiments, the features of the sensor 12 as provided herein may be incorporated into sensors for use on other tissue locations, such as the back, the stomach, the heel, the ear, an arm, a leg, or any other appropriate measurement site. In addition, although the exemplary embodiment of the patient monitoring system 10 illustrated in FIG. 1 may relate to photoplethysmography or regional oximetry, the system 10 may be configured to obtain a variety of medical measurements with a suitable medical sensor. For example, the system 10 may additionally be configured to determine patient electroencephalography or any other desired physiologic parameter. Further, other suitable sensors that may be coupled to the system 10 may include pulse oximetry sensors. One skilled in the art may contemplate any type of a plurality of different sensors coupled to the system 10 for monitoring and/or measuring any number of different physiologic parameters.

As noted, the system 10 includes the sensor 12 that is operably coupled to a patient monitor 14. The monitor 14 may be any type of monitor, for example, any type of instrument or device or display for observing, checking, or keeping a record (continuous or intermittent) of a process or quantity or variables or parameters that are measured and/or monitored. Although only one sensor 12 is shown coupled to the monitor 14 in FIG. 1, in other embodiments, two, three, four, or more sensors 12 may be coupled to the monitor 14. For example, two sensors 12 may be used for cerebral oximetry and simultaneously two other sensors 12 may be used for somatic oximetry or pulse oximetry. As shown in FIG. 1, the sensor 12 includes an emitter 16 and a pair of detectors 18. The emitter 16 and detectors 18 of the sensor 12 are coupled to the monitor 14 via a cable 26 coupled to the monitor 14. The cable 26 may interface directly with the sensor 12 and may include a plurality of conductors (e.g., wires). As described below, the sensor 12 may be configured to store patient-related data, such as, but not limited to, historical regional oximetry data or trend data. Of course, of skilled in the art may contemplate storing any type of patient related data obtained or acquired via any types of sensors without limitation.

The monitor 14 includes a monitor display 20 configured to display information regarding physiologic parameters monitored by the sensor 12, information about the system, and/or alarm indications. The monitor 14 may include various input components 22, such as knobs, switches, keys and keypads, buttons, etc., to provide for operation and configuration of the monitor 14. The monitor 14 also includes a processor (not shown) that may be used to execute code, as defined further below, such as code for implementing various monitoring functionalities enabled by the sensor 12. As described below, for example, the monitor 14 may be configured to process signals generated by the detectors 18 to estimate the amount of oxygenated vs. de-oxygenated hemoglobin in a monitored region of the patient. Of course, any type of physiologic parameters may be monitored and/or measured and/or stored.

The monitor 14 may be any suitable monitor, such as, but not limited to, an INVOS® System monitor available from, for example, Somanetics. However, one skilled in the art may use any type of monitor, as described above. Furthermore, to upgrade conventional operation provided by the monitor 14 to provide additional functions, the monitor 14 may be coupled to a multi-parameter patient monitor 34 via a cable 36 connected to a sensor input port. In addition to the monitor 14, or alternatively, the multi-parameter patient monitor 34 may be configured to calculate physiologic parameters and to provide a central display 38 for the visualization of information from the monitor 14 and from other medical monitoring devices or systems. The multi-parameter monitor 34 includes a processor (not shown) that may be configured to execute code, as defined further below. The multi-parameter monitor 34 may also include various input components 40, such as knobs, switches, keys and keypads, buttons, etc., to provide for operation and configuration of the a multi-parameter monitor 34. In addition, the monitor 14 and/or the multi-parameter monitor 34 may be connected to a network to enable the sharing of information with servers or other workstations.

In certain embodiments, the sensor 12 may be a wireless sensor 12. Accordingly, the wireless sensor 12 may establish a wireless communication with the patient monitor 14 and/or the multi-parameter patient monitor 34 using any suitable wireless standard. By way of example, the wireless module may be capable of communicating using one or more of the ZigBee® standard, WirelessHART standard, BLUETOOTH® standard, IEEE 802.11x standards, or MiWi standard.

The sensor 12 may be configured to perform, for example, regional oximetry. In regional oximetry, by comparing the relative intensities of light received at two or more detectors, it is possible to estimate the blood oxygen saturation of hemoglobin in a region of a body. For example, a regional oximeter may include a sensor to be placed on a patient's forehead and may be used to calculate the oxygen saturation of a patient's blood within the venous, arterial, and capillary systems of a region underlying the patient's forehead (e.g., in the cerebral cortex).

Figure 2:
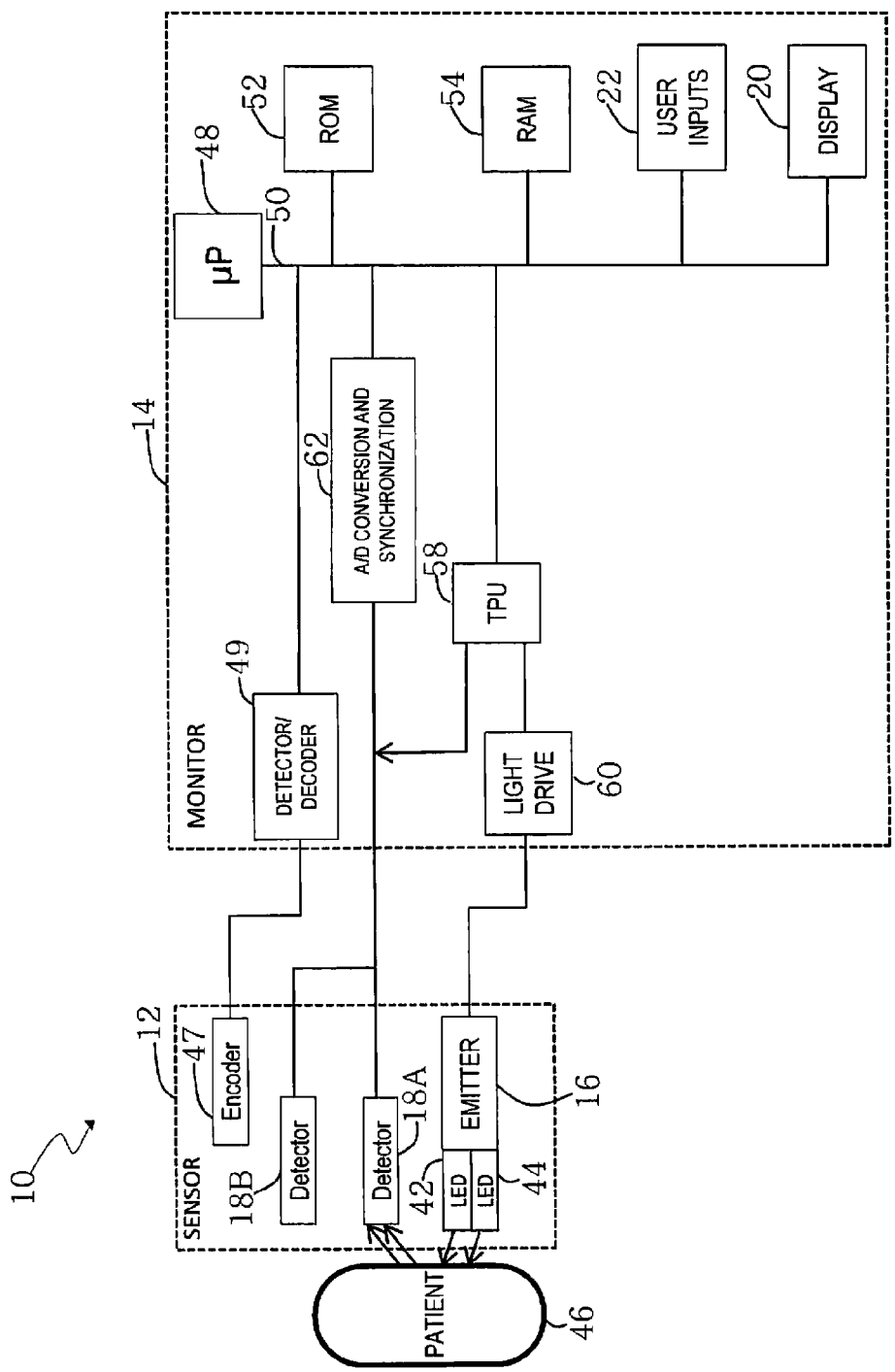
FIG. 2 is a block diagram of the monitoring system of FIG. 1, in accordance with an aspect of the present disclosure.

As illustrated in FIGS. 1 and 2, the sensor 12 may include the emitter 16 and the two detectors 18. One detector 18A that is relatively "close" to the emitter 16 and another detector 18B that is relatively "far" from the emitter 16. Light intensity of one or more wavelengths may be received at both the "close" and the "far" detectors 18A and 18B. Thus, the detector 18A may receive a first amount of light and the detector 18B may receive a second amount of light. Each of the detectors 18 may generate signals indicative of their respective amounts of light. For example, the resulting signals may be contrasted to arrive at a regional saturation value that pertains to additional tissue through which the light received at the "far" detector 18B passed (tissue in addition to the tissue through which the light received by the "close" detector 18A passed, e.g., the brain tissue) when it was transmitted through a region of a patient (e.g., a patient's cranium). Surface data from the skin and skull is subtracted out to produce a regional oxygen saturation ($rSO_2$) value for deeper tissues.

Turning to FIG. 2, a simplified block diagram of the medical system 10 of FIG. 1 is illustrated in accordance with an exemplary embodiment of the present disclosure. The sensor 12 may include optical components in the forms of the emitter 16 and detectors 18A, 18B. The emitter 16 and the detectors 18A, 18B may be arranged in a reflectance or transmission-type configuration with respect to one another. However, in embodiments in which the sensor 12 is configured for use on a patient's forehead, the emitter 16 and detectors 18A, 18B may be in a reflectance configuration.

An emitter 16 may also be at least a light emitting diode, superluminescent light emitting diode, a laser diode, or a vertical cavity surface emitting laser (VCSEL). An emitter 16 and the detectors 18A, 18B may also include optical fiber sensing elements. An emitter 16 may include a broadband or "white light" source, in which case the detectors 18A, 18B could include any of a variety of elements for selecting specific wavelengths, such as reflective or refractive elements or interferometers. These kinds of emitters and/or detectors would typically be coupled to the sensor 12 via fiber optics. Alternatively, the sensor 12 may sense light detected from tissue at a different wavelength from the light emitted into tissue. Such sensors may be adapted to sense, for example, at least fluorescence, phosphorescence, Raman scattering, Rayleigh scattering and multi-photon events, or photoacoustic effects. In one exemplary embodiment, the emitter 16 may be configured for use in a regional saturation technique. To that end, the emitter 16 may include two light emitting diodes (LEDs) 42 and 44 that are capable of emitting at least two wavelengths of light, e.g., red or near infrared light.

In one embodiment, LEDs 42 and 44 emit light in the range of about 600 nm to about 1000 nm. In a particular embodiment, LED 42 is capable of emitting light at about 730 nm and LED 44 is capable of emitting light at about 810 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In any suitable configuration of the sensor 12 may be employed, the detectors 18A and 18B may be an array of detector elements that may be capable of detecting light at various intensities and wavelengths. In one exemplary embodiment, light enters the detector 18 (e.g., detector 18A or 18B) after passing through tissue of a patient 46. In another exemplary embodiment, light emitted from the emitter 16 may be reflected by elements in the patent's tissue to enter the detector 18. The detector 18 may convert the received light at a given intensity, which may be directly related to the absorbance and/or reflectance of light in tissue of the patient 46, into an electrical signal. That is, when more light at a certain wavelength is absorbed, less light of that wavelength is typically received from the tissue by the detector 18, and when more light at a certain wavelength is reflected, more light of that wavelength is typically received from the tissue by the detector 18. After converting the received light to an electrical signal, the detector 18 may send the signal to the monitor 14, where physiologic characteristics may be calculated based at least in part on the absorption and/or reflection of light by tissue of the patient 46.

In certain exemplary embodiments, the medical sensor 12 may also include an encoder 47 that may provide signals indicative of the wavelength of one or more light sources of the emitter 16, which may allow for selection of appropriate calibration coefficients for calculating a physiologic parameter, such as, but not limited to, blood oxygen saturation. The encoder 47 may, for instance, include a coded resistor, an electrically erasable programmable read only memory (EEPROM), or other coding device (such as a capacitor, inductor, programmable read only memory (PROM), RFID, parallel resident currents, or a colorimetric indicator) that may provide a signal to a microprocessor 48 related to the characteristics of the medical sensor 12 to enable the microprocessor 48 to determine the appropriate calibration characteristics of the medical sensor 12. Further, the encoder 47 may include encryption coding that prevents a disposable part of the medical sensor 12 from being recognized by a microprocessor 48 unable to decode the encryption. For example, a detector/decoder 49 may translate information from the encoder 47 before the processor 48 may properly handle it. In some embodiments, the encoder 47 and/or the detector/decoder 48 may not be present.

In certain embodiments, the sensor 12 may include circuitry that stores patient-related data or calibration data and provides the data when requested. The circuitry may be included in the encoder 47 or in separate memory circuitry within the sensor 12. Examples of memory circuitry include, but are not limited to, a random access memory (RAM), a FLASH memory, a PROM, an EEPROM, a similar programmable and/or erasable memory, any kind of erasable memory, a write once memory, or other memory technologies capable of write operations. In one embodiment, patient-related data, such as the $rSO_2$ baseline, trending data, or patient monitoring parameters, may be actively stored in the encoder 47 or memory circuitry. As the patient 46 and sensor 12 travel through a medical facility, such as a hospital, and consequently communicate with different monitors 14, the patient-related data may be read from the encoder 47 and displayed on the monitor display 20 for viewing or used by the monitor 14 for other purposes.

Returning to FIG. 2, signals from the detector 18 and/or the encoder 47 may be transmitted to the monitor 14. By way of example, the monitor 14 shown in FIG. 2 may be an INVOS® System monitor 14 available from Somanetics. The monitor 14 may include one or more processors 48 coupled to an internal bus 50. Also connected to the bus 50 may be a ROM memory 52, a RAM memory 54, and the display 20. A time processing unit (TPU) 58 may provide timing control signals to light drive circuitry 60, which controls when the emitter 16 is activated, and if multiple light sources are used, the multiplexed timing for the different light sources. The received signal from the detector 18 may be passed through analog-to-digital conversion and synchronization 62 under the control of timing control signals from the TPU 58. Specifically, the signal may undergo synchronized demodulation and optionally amplification and/or filtering. However, one skilled in the art may contemplate any other alternative configuration.

For example, LEDs 42 and 44 may be driven out-of-phase, sequentially and in an alternating manner with one another (i.e., only one of LEDs 42 and 44 being driven during the same time interval) such that the detector 18 receives only resultant light spectra emanating from one LED at a time. Demodulation 62 of the signal enables the data associated with LEDs 42 and 44 to be distinguished from one another. After demodulation, the digital data may be downloaded to the RAM memory 54. The digital data may include time stamp information that facilitates appropriate time alignment with other data displayed by the multi-parameter monitor 34.

In an exemplary embodiment, based at least in part upon the received signals corresponding to the light received by detector 18, the processor 48 may calculate the oxygen saturation using various algorithms. These algorithms may use coefficients, which may be empirically determined. For example, algorithms relating to the distance between an emitter 16 and various detector elements in a detector 18 may be stored in the ROM memory 52 and accessed and operated according to processor 48 instructions.

Furthermore, one or more functions of the monitor 14 may also be implemented directly in the sensor 12. For example, in some embodiments, the sensor 12 may include one or more processing components capable of calculating the physiologic characteristics from the signals obtained from the patient 46. In accordance with the present techniques, the sensor 12 may be configured to provide desired contact between the patient 46 and the detector 18, and/or the emitter 16. The sensor 12 may have varying levels of processing power, and may output data in various stages to the monitor 14, either wirelessly or via the cable 26. For example, in some exemplary embodiments, the data output to the monitor 14 may be analog signals, such as detected light signals or processed data.

Figure 3:
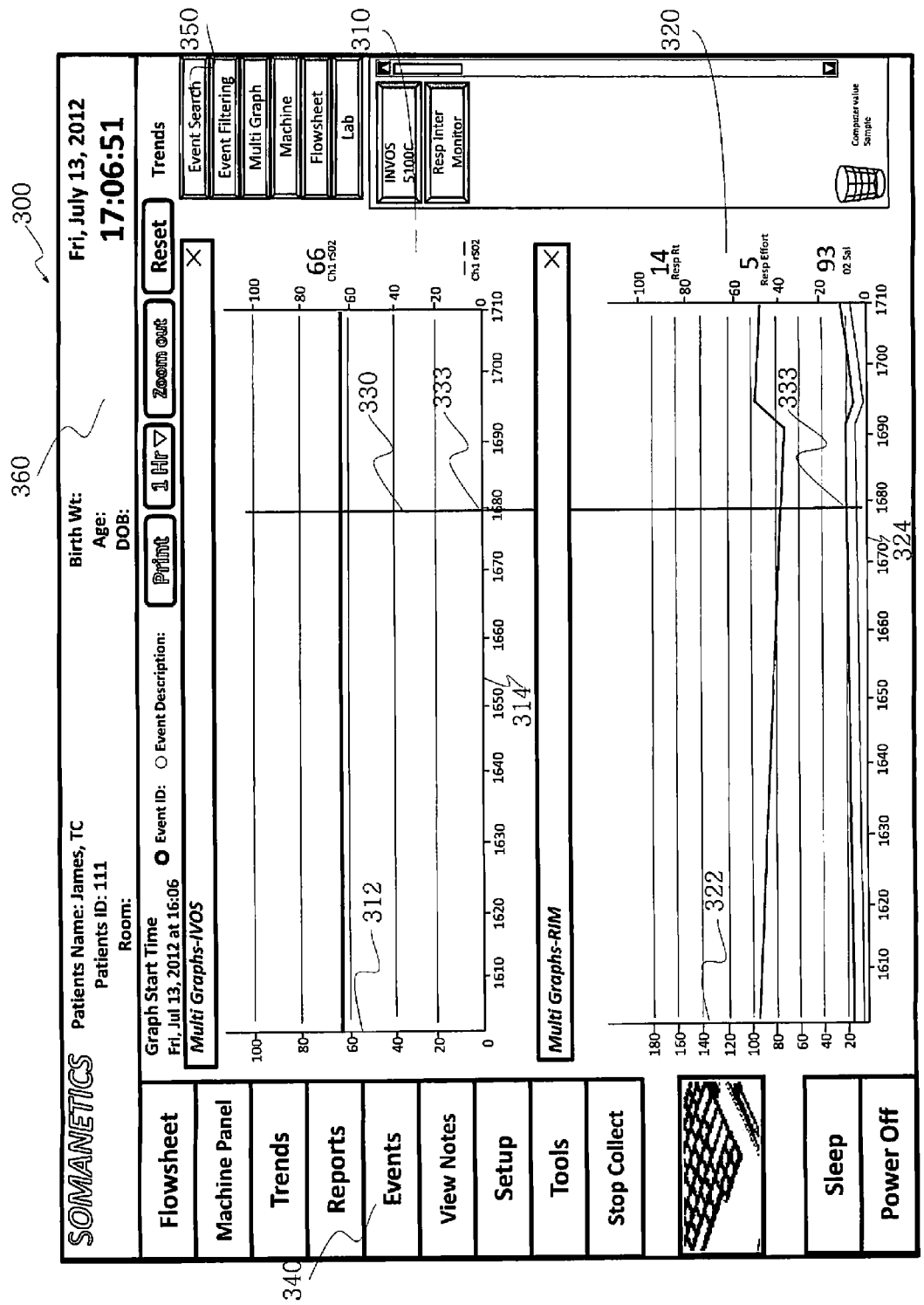
FIG. 3 is a display screen showing a regional oxygen saturation ($rSO_2$) graph and a respiration graph including a time alignment scroll bar, in accordance with an aspect of the present disclosure.

The use of two or more sensors 12 for dual or bilateral examination may provide useful comparative display formats, as illustrated in FIG. 3 and described in greater detail below.

FIG. 3 illustrates a display screen 300 showing a regional oxygen saturation ($rSO_2$) graph 310 and a respiration graph 320, in accordance with the embodiments of the present disclosure. The y-axis 312 of the $rSO_2$ graph 310 represents oxygen saturation values, whereas the x-axis 314 of the $rSO_2$ graph 310 represents time values. The y-axis 322 of the respiration graph 320 represents oxygen respiratory values, whereas the x-axis 324 of the respiration graph 320 represents time values. It is noted that multiple y-axes may be on a single graph, and depending on the parameter being monitored they may share a y-axis where the range of values is relatively common, as shown in graph 320. The graphs 310, 320 may be referred to as "stacked" graphs. In other words, the graphs 310, 320 are positioned on top of each other, in a vertical configuration or orientation, and in a non-overlapping manner to create a "stacked" effect. A marker 330 or vertical time scroll bar extends across the two graphs 310, 320. The marker 330 crosses or intersects the x-axes 314, 324 of both graphs 310, 320 at a common point 333. This is achieved due to the time alignment of the graphs 310, 320 on the x-axes 312, 314. In use or operation, moving the marker 330 from a first point in time to a second point in time for one physiologic parameter causes corresponding changes to other physiologic parameters from the first point in time to the second point in time.

Additionally, the left hand portion of the display screen 300 depicts a first set of buttons 340, whereas the right hand portion of the display screen 300 depicts a second set of buttons 350. The functions of the first set of buttons 340 may relate to "Trends," "Reports," "Events," "View Notes," "Setup," "Tools," "Sleep", and "Power Off," to name a few examples. The functions of the second set of buttons 350 may relate to "Event Search," "Event Filtering," "Multi-Graph," "Flow Sheet," to name a few examples. Of course, one skilled in the art may contemplate using a plurality of different buttons that provide for a plurality of different functions/operations to be activated or triggered by a medical professional. Moreover, a top area 360 of the display screen 300 may be used to display patient information, such as the name, age, and date of birth of the patient. Of course, any type of patient data may be displayed on the top area 360.

In an alternative embodiment, one skilled in the art may contemplate stacking a plurality of graphs on top of each other, in a vertical configuration and non-overlapping manner, via a plurality of columns. In particular, it is contemplated that the plurality of charts/graphs are stacked in, for example, two columns. For example, one stacked column may include three charts/graphs and a second stacked column, directly adjacent the first column, may include another three charts/graphs. Each stacked column may include its own vertical marker. For example, an acute event may have occurred for a patient at 1:00 pm and another acute event may have occurred for the same patient at 5:00 pm during the day. Thus, the medical professional may display physiologic conditions on a first column relating to the 1:00 pm acute event and display physiologic conditions on a second column, adjacent or abutting the first column, relating to the 5:00 pm acute event. A vertical first marker may be generated for the first stacked column, whereas a second vertical marker may be generated for the second stacked column. The medical professional may then align the time axes of the first column and the second column in order to compare the measured physiologic conditions for both events simultaneously. The above example is merely a non-limiting example for illustrative purposes. One skilled in the art may contemplate a plurality of different visual configurations for displaying a plurality of graphs with one or more vertical markers.

With further reference to FIG. 3, the output from sensors 12 (see FIG. 1) is separately processed to provide a particular regional oxygen saturation value, and these regional values are separately displayed on the monitor display 20 as both a numeric or other such quantified value, constituting basically an instantaneous real-time value, and as a point in a graphical plot, representing a succession of such values taken over time. As illustrated, the charts/graphs 310, 320 may advantageously be disposed one above the other in direct time alignment, for convenient examination and comparison. While the instantaneous numeric displays provide useful information, particularly when arranged in the manner illustrated in FIG. 3, the graphical trace displays also provide useful information by directly showing the ongoing trend, and doing so in a contrasting, comparative manner, as well as showing the actual or relative values.

As a result, a medical professional may scroll over the graphs 310, 320 via the vertical marker 330 to view the corresponding patient data or information. In use, this may assist a medical professional to visualize activity of a patient over a given time displayed on the display screen 300, and scroll to particular points that the medical professional desires to view so that the medical professional may make a determination of the severity of an acute event that previously occurred, or otherwise assess any number of alarming conditions of the physiologic parameters.

Scroll bar 330 is configured to enable a medical professional to scroll through the images or plots or charts/graphs displayed on the display screen 300. Scrolling through the charts/graphs 310, 320 with the scroll bar 330 causes a change in the data displayed. For example and without limitation, a user may manipulate the scroll bar 330, by moving it horizontally to the left or to the right, to control only certain areas or portions appearing on the display screen 300. It is also envisioned that a user may manipulate the placement of the scroll bar 330, or otherwise rearrange any of the graphs 310, 320 displayed on the display screen 300. Additionally, or alternatively, any of the physiologic parameters appearing on the display screen 300 may be scrollable by a user swiping across the particular data displayed, as is well known in the area of user manipulable graphical displays.

Figure 4:
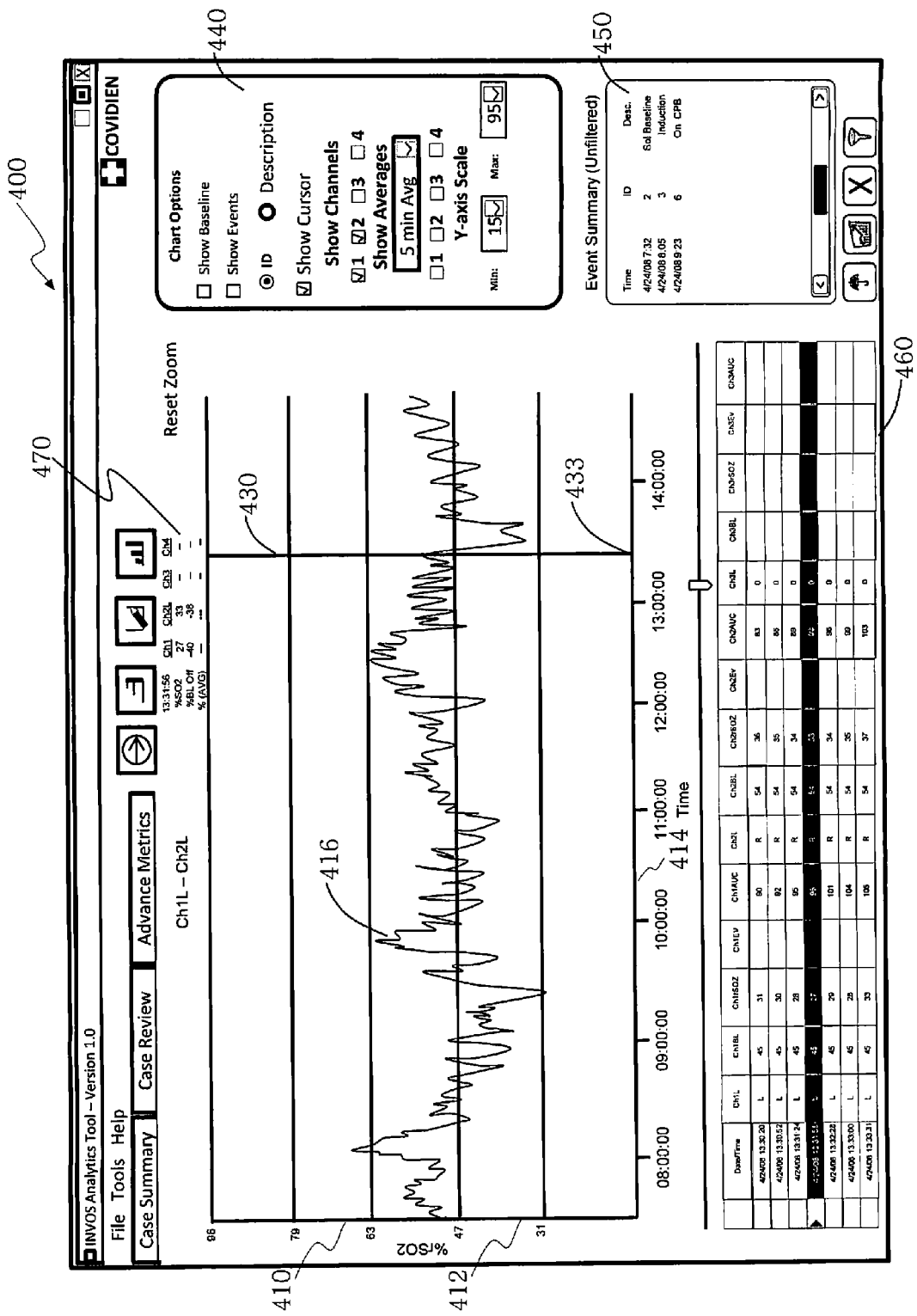
FIG. 4 is a display screen illustrating a regional oxygen saturation ($rSO_2$) graph with a time scroll bar, in accordance with an aspect of the present disclosure.

FIG. 4 illustrates a display screen 400 illustrating a regional oxygen saturation ($rSO_2$) graph 410 with a time scroll bar or marker 430, in accordance with an aspect of the present disclosure.

The y-axis 412 of the regional oxygen saturation graph 410 represents regional oxygen saturation values, whereas the x-axis 414 of the regional oxygen saturation graph 410 represents time values. The plot 416 illustrates the variation of the regional oxygen saturation values during a given time period. A marker 430 or vertical time scroll bar extends across the graph 410. The marker 430 crosses or intersects the x-axis 414 of graph 410 at a point 433. Additionally, the top right hand portion of the display screen 400 depicts a first set of buttons/selections 440, whereas the bottom right hand portion of the display screen 400 depicts data readout 450. The first set of buttons/selections 440 may relate to chart option functions/operations, whereas data readout 450 may relate to event summary functions/operations. Of course, one skilled in the art may contemplate using a plurality of different buttons that provide for a plurality of different functions/operations to be activated by a medical professional.

Moreover, a bottom portion 460 may include a list of other physiologic parameter values recorded at time point 433 for comparison with the $rSO_2$ value at point 433. Thus, the medical professional may compare physiologic parameter values at point of time 433 to the regional oxygen saturation at point of time 433. In other words, instead of stacking graphs on the display screen 400, a medical professional may display only one graph of one physiologic parameter and compare it to other physiologic parameters listed in area 460. As the medical professional horizontally moves the marker 430 across the time axis 414, area 460 is also automatically updated, in real-time, to correspond to the time value selected by the medical professional.

Therefore, the physiologic values listed in area 460 are updated in real-time based on movement of the marker 430. Every point in time on the x-axis 414 renders a different set of values for all the other physiologic values monitored/measured. Thus, in use or operation, moving the marker 430 from a first point in time to a second point in time for one physiologic parameter causes corresponding changes to other physiologic parameters from the first point in time to the second point in time. Further, a top portion 470 may include further parameter data/information, such as averages or differences of parameters during specific time ranges or points in time.

Therefore, according to FIGS. 3 and 4, the aligned data or information or measured parameters collected by the sensors 12 (see FIG. 1) may be aligned according to time stamp information for data or information or measured parameters, as also occurs in FIGS. 5 and 6 described below. Moreover, a medical professional is permitted to move the marker 330, 430 to a previous measured time period or point in time 333, 433 corresponding to historical medical events of interest (or acute events) for evaluating the measured physiologic parameters during that measured time period or point in time. Stated differently, as the marker 330, 430 is moved across one graph of the plurality of graphs to a prior point in time 333, 433, all the measured physiologic parameters of all of the plurality of graphs displayed on a monitor 14, for example, an oximetry monitor, at that prior point in time are configured to be simultaneously evaluated and/or analyzed. Thus, a direct relationship is established between all the physiologic parameters at any given point in time on the x-axes 314, 414, based on movement of the marker 330, 430 across the time axes 314, 414. It is noted that any type of monitor may be used and that the exemplary embodiments of the present disclosure are not limited to an oximetry monitor.

Figure 5:
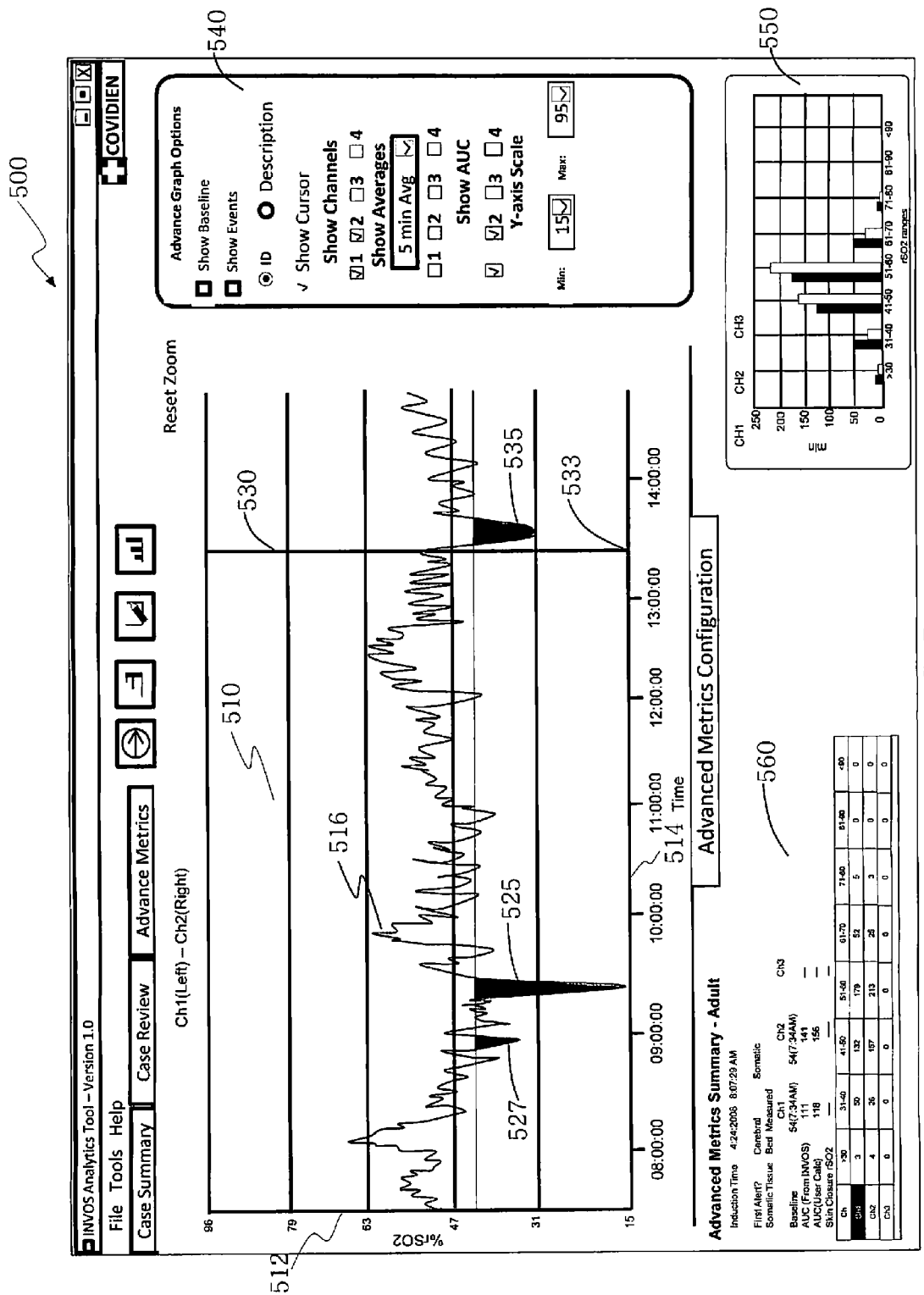
FIG. 5 is a display screen illustrating a regional oxygen saturation ($rSO_2$) graph showing selected peaks and valleys for further analysis, in accordance with an aspect of the present disclosure.

FIG. 5 is a display screen 500 illustrating a regional oxygen saturation ($rSO_2$) graph 510 showing selected peaks or valleys 525, 527, 535, in accordance with an aspect of the present disclosure. In FIG. 5, the regional saturation graph 510 depicts one or more areas 525, 527, 535 under a curve or peak that may be selected (e.g., via the time scroll bar 530) for further analysis. The y-axis 512 of the $rSO_2$ graph 510 represents oxygen saturation values, whereas the x-axis 514 of the $rSO_2$ graph 510 represents time values. The plot 516 illustrates the variation of the oxygen saturation values during a given time period. A marker 530 or vertical time scroll bar extends across the graph 510. The marker 530 crosses or intersects the x-axis 514 of graph 510 at a point 533. In FIG. 5, areas 525, 527, 535, which are under a curve or in a downward region of plot 516 are highlighted. A medical professional may zoom into areas 525, 527, 535 and move the vertical marker 530 toward those regions to further evaluate and/or analyze the areas 525, 527, 535. These areas 525, 527, 535 may be highlighted in different colors or different patterns to indicate different conditions to the medical professional.

Additionally, the top right hand portion of the display screen 500 depicts a set of buttons 540, whereas the bottom right hand portion of the display screen 500 depicts a bar chart 550. The set of buttons 540 may relate to chart option functions/operations, whereas the bar chart 550 may relate to $rSO_2$ ranges during various measured and/or monitored time periods. Of course, one skilled in the art may contemplate using a plurality of different buttons that provide for a plurality of different functions/operations to be activated by a medical professional. Moreover, a bottom portion 560 may include a list of physiologic parameter values recorded at time point 533. Thus, the medical professional may compare other measured physiologic parameter values at point of time 533 to the regional oxygen saturation at point of time 533.

As in FIG. 4, not all of the physiologic parameters need to be plotted in order to perform comparisons between the physiologic parameters for a common point in time or common time interval. As the medical professional horizontally moves the marker 530 across the time axis 514, area 560 is also automatically updated, in real-time, to correspond to the time value selected by the medical professional. Every point in time on the x-axis 514 renders a different set of values for all the other physiologic values monitored/measured. Therefore, the physiologic values listed in area 560 are constantly and continuously updated in real-time based on the movement of the marker 530. In use or operation, moving the marker 530 from a first point in time to a second point in time for one physiologic parameter causes corresponding updates to other corresponding physiologic parameters from the first point in time to the second point in time.

Figure 6:
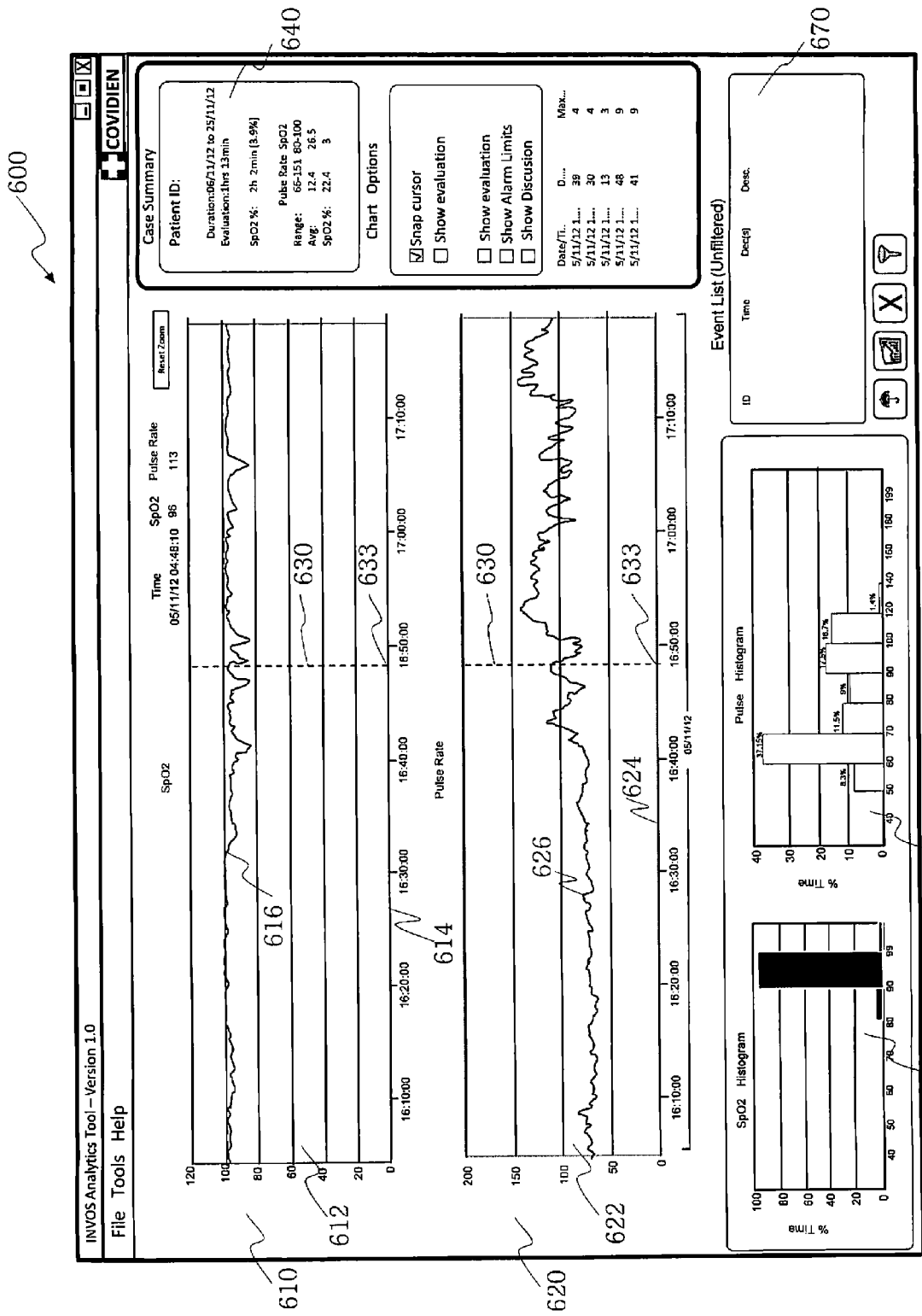
FIG. 6 is a display screen showing a regional oxygen saturation ($rSO_2$) graph and a respiration graph including a time alignment scroll bar, as well as histograms generated from scrolling the time alignment scroll bar along various points of the graphs, in accordance with an aspect of the present disclosure.

FIG. 6 illustrates a display screen 600 showing a regional oxygen saturation (rSO$_2$) graph 610 and a pulse rate graph 620 including a time alignment scroll bar 630, in accordance with an aspect of the present disclosure.

In FIG. 6, the pulse oximetry graph 610 is time aligned with the pulse rate graph 620. The marker or time scroll bar 630 extends through both of the graphs 610, 620. The y-axis 612 of the rSO$_2$ graph 610 represents oxygen saturation values, whereas the x-axis 614 of the rSO$_2$ graph 610 represents time values. The y-axis 622 of the pulse rate graph 620 represents oxygen respiratory values, whereas the x-axis 624 of the pulse rate graph 620 represents time values. The graphs 610, 620 may be referred to as "stacked" graphs. In other words, the graphs 610, 620 are positioned on top of each other, in a vertical configuration or orientation, and in a non-overlapping manner to create a "stacked" effect. A marker 630 or vertical time scroll bar extends across the two plots 616, 626 of graphs 610, 620. The marker 630 crosses or intersects the x-axes 614, 624 of both graphs 610, 620 at a common time data point 633.

Additionally, the right hand portion of the display screen 600 depicts a data summary window 640. The data summary window 640 may relate to chart option functions/operations. Of course, one skilled in the art may contemplate using a plurality of different buttons that provide for a plurality of different functions/operations to be activated by a medical professional. Moreover, a first bottom area 650 may depict a histogram based on the rSO$_2$ graph 610 and a second bottom area 660 may depict a histogram based on the pulse rate graph 620. Thus, the medical professional may compare at least the two parameters (i.e., oxygen saturation and pulse rate) at a common point in time 633 by moving the vertical marker 633 across the length of the times axes 614, 624. This is achieved due to the time alignment of the graphs 610, 620 on the x-axes 612, 614. This information may be extracted and depicted as histograms in areas 650, 660. Of course, one skilled in the art may contemplate any type of visual configuration to display data/information related to any physiologic parameters selected by a medical professional. Further, an event list area 670 may be provided at the bottom right hand portion of the screen 600. This area 670 may indicate various time periods where events of interest took place in order to prompt the medical professional to look into those points in time for further examination. Area 670 may present a summary display of all prior points of interest for any period of time.

Figure 7:
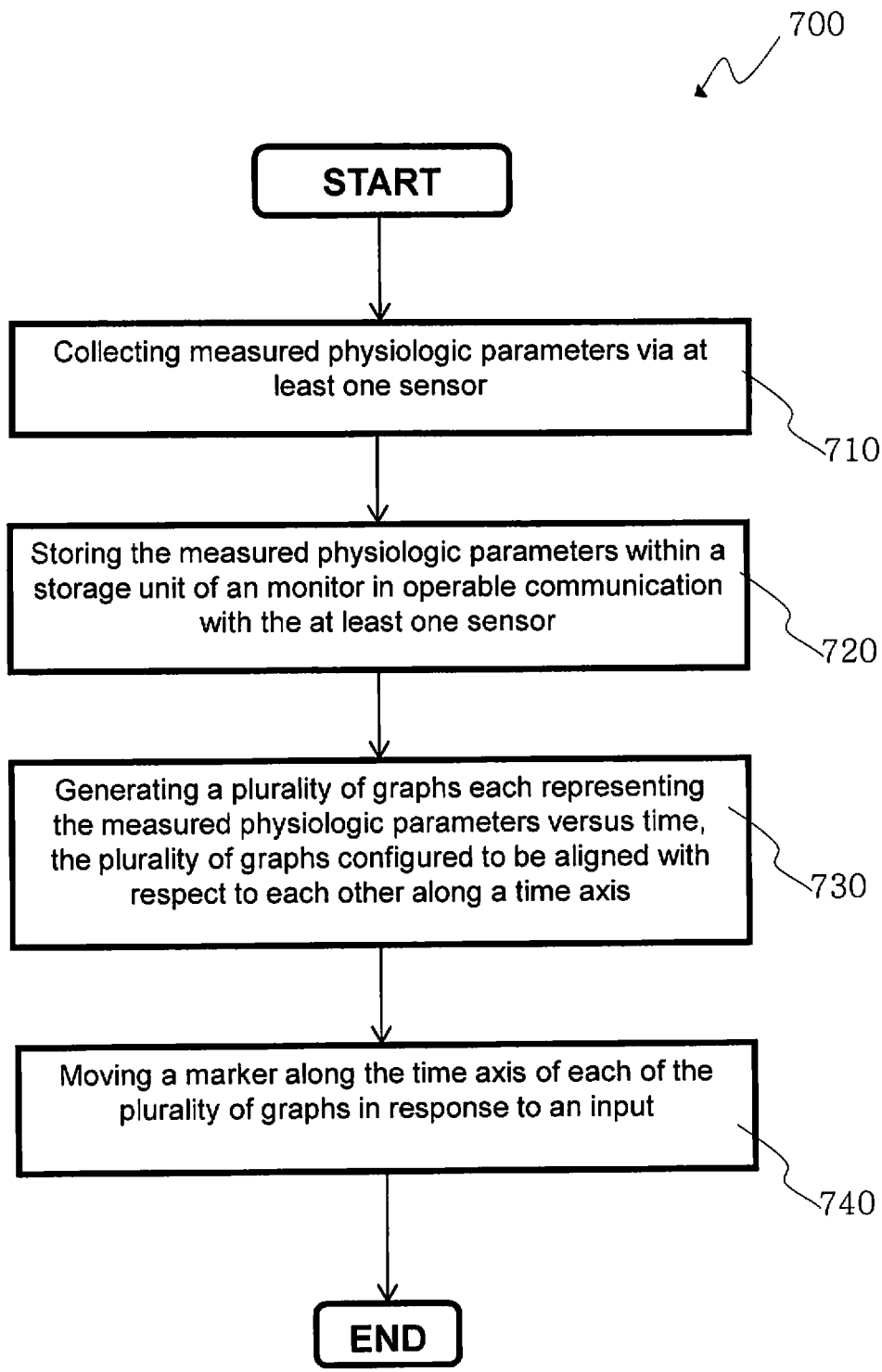
FIG. 7 is a flowchart illustrating a method of measuring changes in site-specific oxygen levels, in accordance with an aspect of the present disclosure.

FIG. 7 is a flowchart 700 illustrating a method of measuring changes in site-specific oxygen levels, in accordance with one embodiment of the present disclosure.

The flowchart 700 includes the following steps. In step 710, measured physiologic parameters are collected via at least one sensor, such as, but not limited to, an oximetry sensor. Of course, none of the exemplary embodiments are limited to any specific sensor. While oximetry sensors are used in this example, the parameters could be any type of patient parameters that a clinician desires to compare to other parameters for a selected time period. In step 720, the measured physiologic parameters are stored within a storage unit of a monitor, for example, an oximetry monitor in operable communication with the at least one sensor. In step 730, a plurality of graphs each representing the measured physiologic parameters versus time are generated, the plurality of graphs configured to be aligned with respect to each other along a time axis. In step 740, a marker is moved along the time axis of each of the plurality of graphs in response to an input. The process then ends. It is to be understood that the method steps described herein need not necessarily be performed in the order as described. Further, words such as "thereafter," "then," "next," etc. are not intended to limit the order of the steps. These words are simply used to guide the reader through the description of the method steps.

In an alternative embodiment, it is noted that the values of the various measured and/or monitored parameters are periodically (or intermittedly) recorded during predefined or predetermined points in time. In other words, it is contemplated that the values are recorded, for example, every few seconds or every few minutes, in order to prevent overflow of data in the storage module from continuous recording of every data point. However, it is also contemplated to continuously record the physiologic parameters in a local or remote data storage unit.

Figure 8:
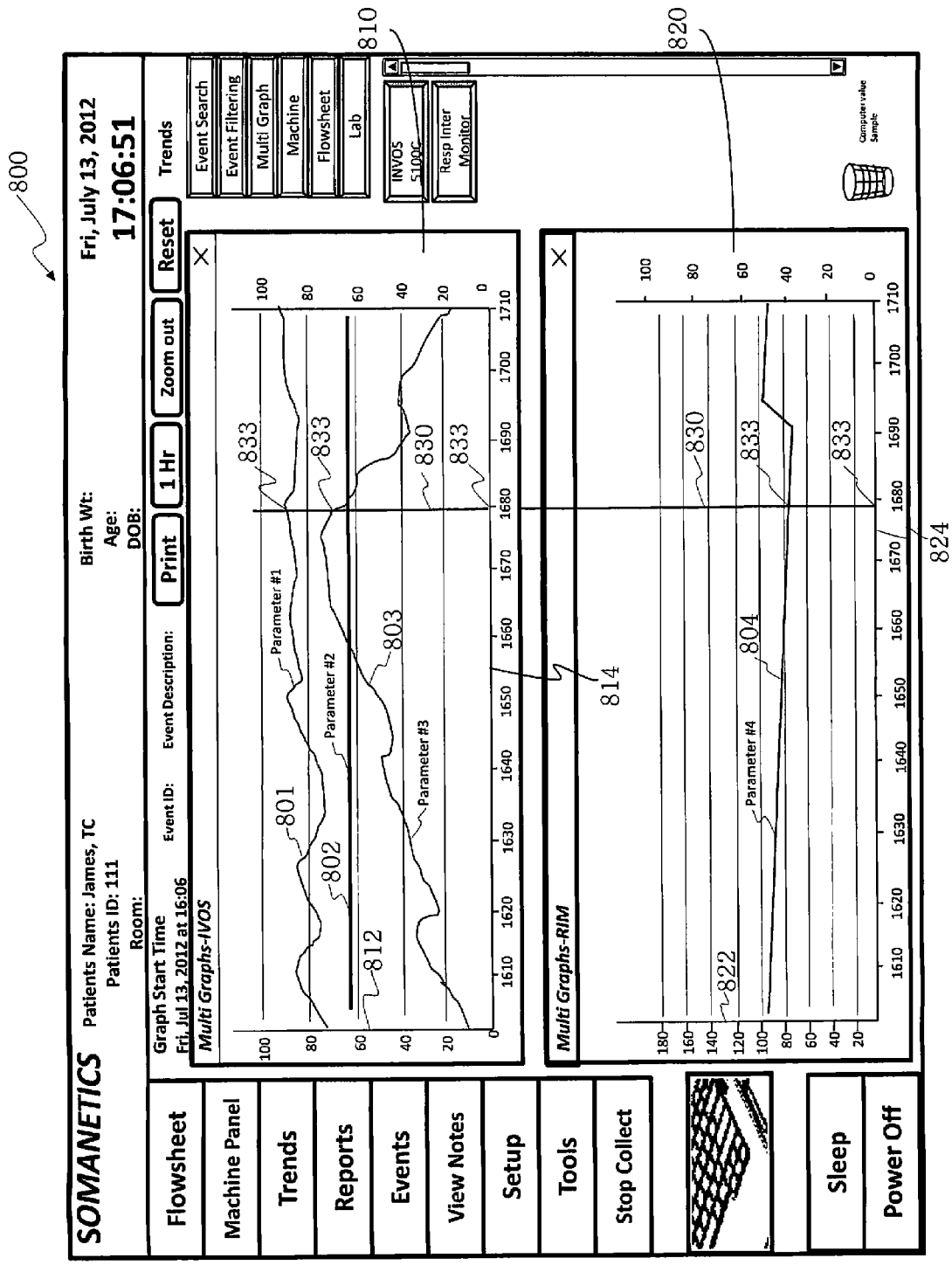
FIG. 8 is a display screen showing a first graph including three different parameters and a second graph including one parameter, with a time alignment scroll bar extending through all four parameters at a common point, in accordance with an aspect of the present disclosure.

FIG. 8 is a display screen 800 showing a first graph 810 including three different parameters and a second graph 820 including one parameter, with a time alignment scroll bar 830 extending through all four parameters at a common point 833, in accordance with an aspect of the present disclosure.

The y-axis 812 of the first graph 810 represents oxygen saturation values, whereas the x-axis 814 of the first graph 810 represents time values. In an instance of multiple parameters on a single graph, the y-axis can be selected in accordance with parameters being displayed and at least two different y-axes can be shown on a single graph. Moreover, when hovering over a point in time, the graph values associated with that point can appear on the graph, say graph 820, as a pop-up. The y-axis 822 of the second graph 820 represents oxygen respiratory values, whereas the x-axis 824 of the second graph 820 represents time values. The graphs 810, 820 may be referred to as "stacked" graphs. In other words, the graphs 810, 820 are positioned on top of each other, in a vertical configuration or orientation, and in a non-overlapping manner to create a "stacked" effect. A marker 830 or vertical time scroll bar extends across the two graphs 810, 820. The marker 830 crosses or intersects the x-axes 814, 824 of both graphs 810, 820 at a common point 833. This is achieved due to the time alignment of the graphs 810, 820 on the x-axes 812, 814.

Additionally, the first graph 810 may include or display, for example, three different parameters, that is, parameters 801, 802, 803. Therefore, multiple parameters may be displayed on a single graph. One skilled in the art may contemplate a number of different parameters to be displayed on each graph 810, 820.

Figure 9:
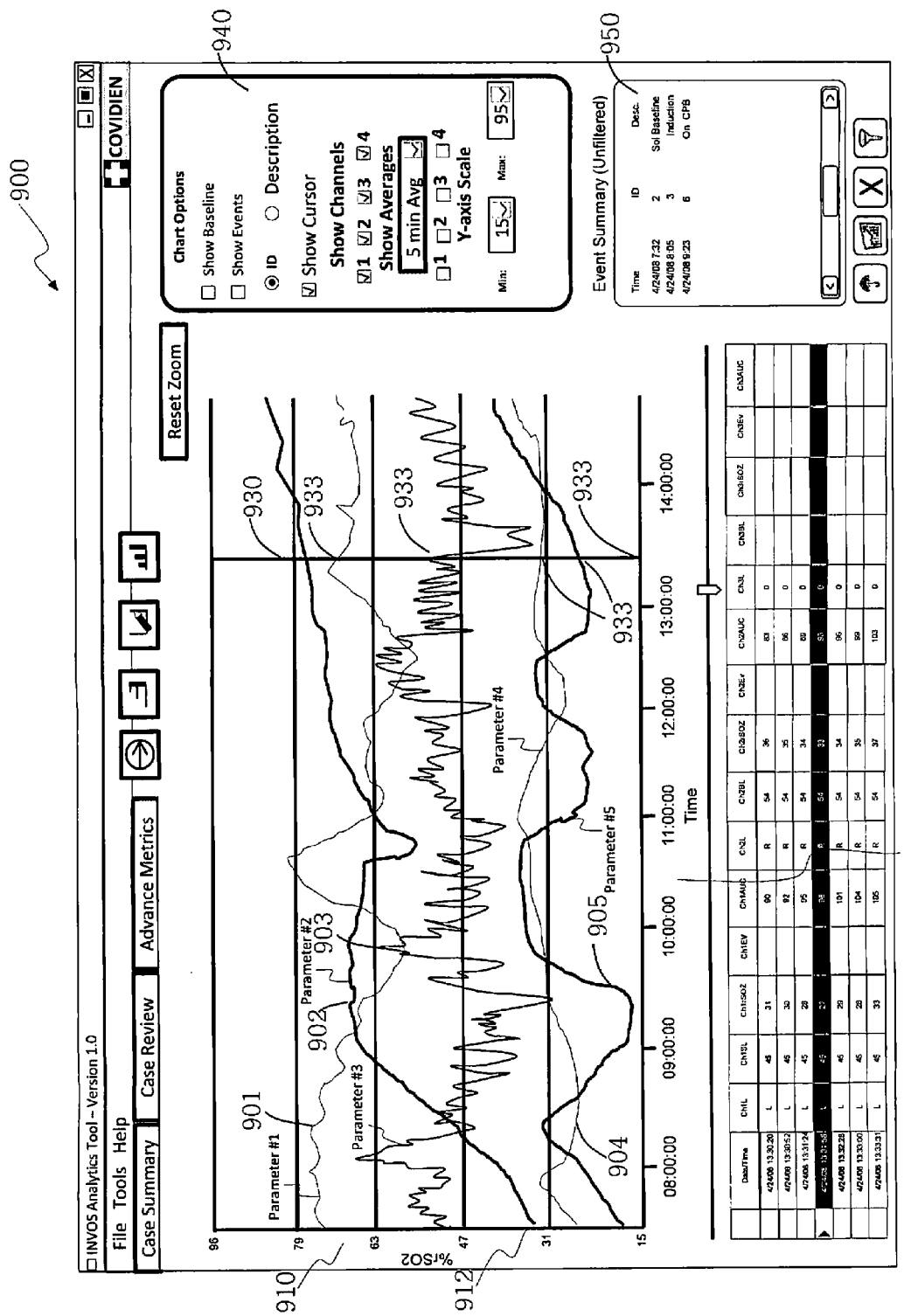
FIG. 9 is a display screen illustrating five lines, each representing a different parameter, with a time scroll bar extending through all five parameters at a common point, in accordance with an aspect of the present disclosure.

FIG. 9 is a display screen 900 illustrating five lines, each representing a different parameter, with a time scroll bar 930 extending through all five parameters at a common point 933, in accordance with an aspect of the present disclosure.

The y-axis 912 of the graph 910 represents regional oxygen saturation values, whereas the x-axis 914 of the graph 910 represents time values. Lines 901, 902, 903, 904, 905 illustrate or represent five different parameters. A marker 930 or vertical time scroll bar extends across or intersects the lines 901, 902, 903, 904, 905. The marker 930 crosses or intersects the x-axis 914 of a common point 933. Therefore, multiple parameters may be displayed on a single graph. One skilled in the art may contemplate a number of different parameters to be displayed on graph 910. For example, six different trend parameters may be displayed on graph 910. However, there is no limit to the number of parameters to be displayed on a single graph.

Additionally, the top right hand portion of the display screen 900 depicts a first set of buttons/selections 940, whereas the bottom right hand portion of the display screen 900 depicts data readout 950. The first set of buttons/selections 940 may relate to chart option functions/operations, whereas data readout 950 may relate to event summary functions/operations. One skilled in the art may contemplate a number of different buttons or selections pertaining to each of the five lines 901, 902, 903, 904, 905.

Figure 10:
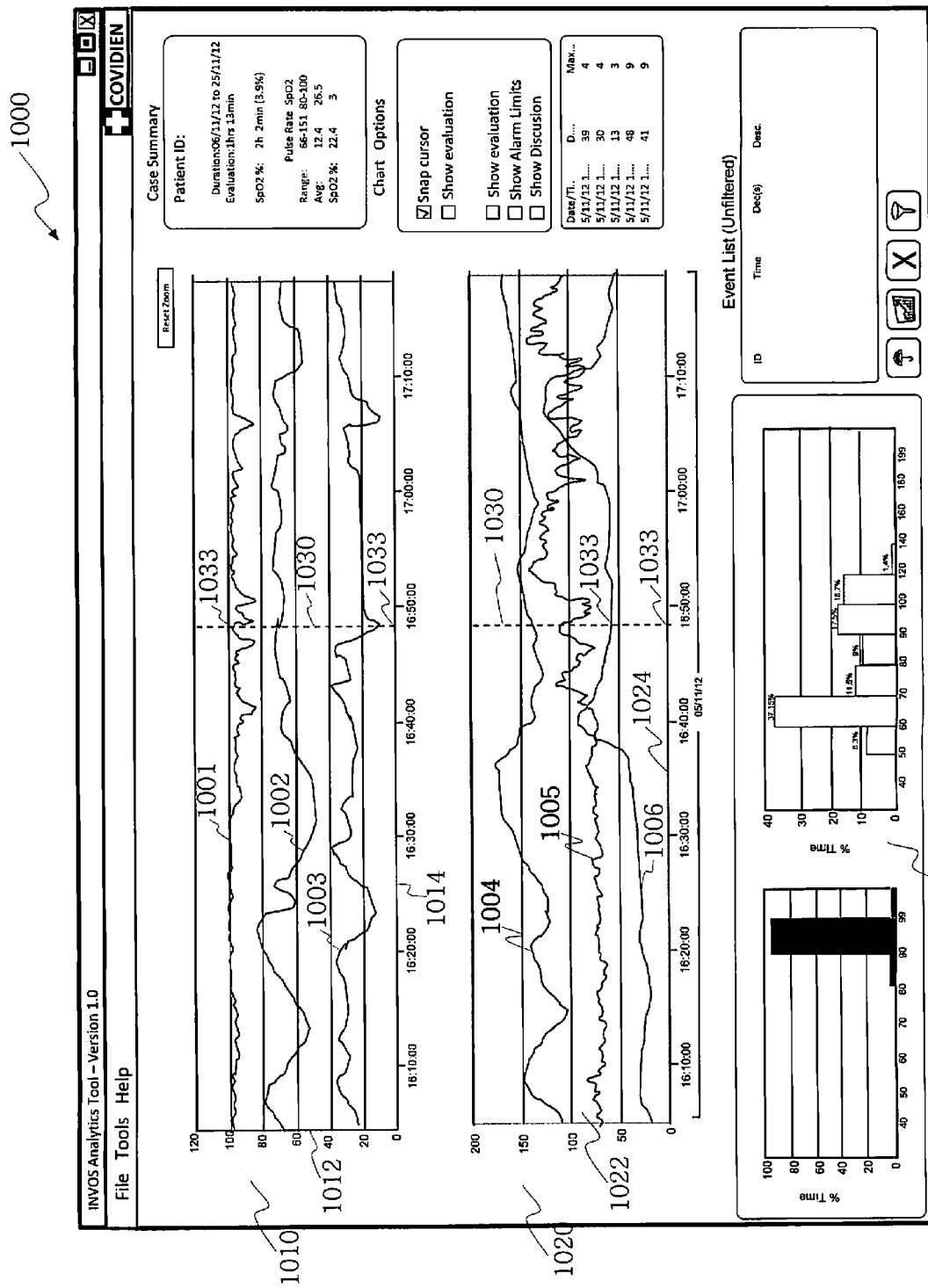
FIG. 10 is a display screen showing a first graph including multiple parameters and a second graph including multiple parameters, where a time alignment scroll bar extends through all the multiple parameters of each of the first and second graphs at a common point, as well as histograms generated from scrolling the time alignment scroll bar along various points of the graphs, in accordance with an aspect of the present disclosure.

FIG. 10 is a display screen 1000 showing a first graph 1010 including multiple parameters and a second graph 1020 including multiple parameters, where a time alignment scroll bar 1030 extends through all the multiple parameters of each of the first and second graphs at a common point 1033, as well as histograms 1050 generated from scrolling the time alignment scroll bar along various points of the graphs, in accordance with an aspect of the present disclosure.

In FIG. 10, the first graph 1010 is time aligned with the second graph 1020. The marker or time scroll bar 1030 extends through both of the graphs 1010, 1020. The y-axis 1012 of the first graph 1010 represents oxygen saturation values, whereas the x-axis 1014 of the first graph 1010 represents time values. The y-axis 1022 of the second graph 1020 represents oxygen respiratory values, whereas the x-axis 1024 of the second graph 1020 represents time values. The graphs 1010, 1020 may be referred to as "stacked" graphs. In other words, the graphs 1010, 1020 are positioned on top of each other, in a vertical configuration or orientation, and in a non-overlapping manner to create a "stacked" effect. A marker 1030 or vertical time scroll bar extends across the lines 1001, 1002, 1003, 1004, 1005, 1006 of graphs 1010, 1020. The marker 1030 crosses or intersects the x-axes 1014, 1024 of both graphs 1010, 1020 at a common time data point 1033. Thus, graph 1010 may include 3 lines representing 3 different parameters, whereas graph 1020 may include 3 lines representing another 3 different parameters. Therefore, 6 different parameters or parameters trends may be monitored at the same time at the common point 1033. One skilled in the art may contemplate displaying and monitoring a number of different parameters on each graph 1010, 1020. Of course, more than 2 graphs may be presented each including a plurality of different parameters. The exemplary embodiments of the present disclosure are not limited to the number of graphs or the number of parameters included in each graph. Additionally, all parameters 1001, 1002, 1003, 1004, 1005 may be represented or displayed in histogram format 1050 illustrated at the bottom of display screen 1000.

In summary, the plurality of graphs are stacked with respect to each other in a vertical orientation and in a non-overlapping manner. The marker is a vertical time scroll bar configured to intersect the plurality of graphs at a common point on the time axis. The marker is moved to a previous measured time period or point in time corresponding to historical medical events (or acute events) of interest for evaluating the measured physiologic parameters during that measured time period or point in time. Also, as the marker is moved across one graph of the plurality of graphs to a point in time, all the measured physiologic parameters of all of the plurality of graphs displayed on the monitor at that point in time are configured to be simultaneously evaluated and/or analyzed. Stated differently, as the marker is moved across one graph of the plurality of graphs to a prior point in time, all the measured physiologic parameters of all of the plurality of graphs displayed on the monitor at that prior point in time are configured to be simultaneously analyzed by, for example, a medical professional. Thus, by moving the marker across a graph of a plurality of graphs, a direct relationship is established between the physiologic parameters at any given point in time on a single display panel. Stated differently, moving the marker from a first point in time to a second point in time for one physiologic parameter causes corresponding updates to the display of other physiologic parameters from the first point in time to the second point in time.

Alternatively or additionally, the data/information, indicators, and/or metrics may be displayed in various forms to the user to assist in determining a screen result or monitoring the patient. Although the processes and methods are described below for exemplary purposes with respect to screening patients, the present disclosure is not limited to screening, as it is contemplated that the aspects and features of the present disclosure be applicable for use in the monitoring of physiologic parametric levels for any suitable purpose. Obviously, the settings, parameters, and thresholds may change depending on a particular purpose. However, the general features and aspects of the present disclosure remain generally consistent regardless of the particular purpose. Further, the features and aspects of the present disclosure may be implemented in system 10 in any suitable fashion, e.g., via the hardware and software configuration of system 10 or using any other suitable software, firmware, and/or hardware.

For instance, when implemented via executable instructions, various elements of the present disclosure are in essence the code defining the operations of such various elements. The executable instructions or code may be obtained from a computer readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, the computer readable media may include any medium that may store or transfer information.

The computer means or computing means or processing means may be operatively associated with the assembly, and is directed by software to compare the first output signal with a first control image and the second output signal with a second control image. The software further directs the computer to produce diagnostic output. Further, a means for transmitting the diagnostic output to an operator of the verification device is included. Thus, many applications of the present disclosure could be formulated. The exemplary network disclosed herein may include any system for exchanging data or transacting business, such as the Internet, an intranet, an extranet, WAN (wide area network), LAN (local area network), satellite communications, and/or the like. It is noted that the network may be implemented as other types of networks.

Additionally, "code" as used herein, or "program" as used herein, may be any plurality of binary values or any executable, interpreted or compiled code which may be used by a computer or execution device to perform a task. This code or program may be written in any one of several known computer languages. A "computer," as used herein, may mean any device which stores, processes, routes, manipulates, or performs like operation on data. A "computer" may be incorporated within one or more transponder recognition and collection systems or servers to operate one or more processors to run the transponder recognition algorithms. Moreover, computer-executable instructions include, for example, instructions and data which cause a general purpose computer, special purpose computer, or special purpose processing device to perform a certain function or group of functions. Computer-executable instructions also include program modules that may be executed by computers in stand-alone or network environments. Generally, program modules include routines, programs, objects, components, and data structures, etc. that perform particular tasks or implement particular abstract data types.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

While several embodiments of the disclosure have been shown in the drawings and described in detail hereinabove, it is not intended that the disclosure be limited thereto, as it is intended that the disclosure be as broad in scope as the art will allow. Therefore, the above description and appended drawings should not be construed as limiting, but merely as exemplifications of particular embodiments. Those skilled in the art will envision other modifications within the scope and spirit of the claims appended hereto.

What is claimed is:

1. A system comprising:
   at least one sensor; and
   a monitor in operable communication with the at least one sensor, the monitor configured to display a plurality of graphs each representing a measured physiologic parameter versus time, the plurality of graphs configured to be aligned with respect to each other along a time axis;
   wherein a marker moves along the time axis of each of the plurality of graphs in response to an input received from an input unit such that the marker intersects the plurality of graphs at a common point on the time axis, and physiologic values at the common point in time of each of the plurality of graphs are displayed on the monitor, continuously and in real-time, as the marker moves across the plurality of graphs.

2. The system according to claim 1, wherein the marker is a time scroll bar.

3. The system according to claim 1, wherein a graph of each measured physiologic parameter is indicative of a trend of the measured physiologic parameter over a period of time.

4. The system according to claim 1, wherein the plurality of graphs are stacked with respect to each other in a vertical orientation and in a non-overlapping manner.

5. The system according to claim 4, wherein the marker is a vertical time scroll bar.

6. The system according to claim 1, wherein the marker is moved to a previous measured time period or point in time corresponding to historical medical events of interest for evaluating the measured physiologic parameters during that measured time period or point in time.

7. The system according to claim 1, wherein the monitor includes a storage module for storing values of the measured physiologic parameters.

8. The system according to claim 7, wherein the values are periodically recorded during predefined points of time.

9. The system according to claim 1, wherein, by moving the marker across a graph of the plurality of graphs, a direct relationship is established between all the physiologic parameters at any given point in time.

10. The system according to claim 1, wherein the measured physiologic parameters include at least one of: oxygen saturation, pulse rate, respiration rate, heart rate, temperature, arterial pressure, blood pressure, and hydration status.

11. A method comprising:
    collecting measured physiologic parameters via at least one sensor;
    storing the measured physiologic parameters within a storage unit of a monitor in operable communication with the at least one sensor; generating a plurality of graphs each representing the measured physiologic parameters versus time, the plurality of graphs configured to be aligned with respect to each other along a time axis;
    moving a marker along the time axis of each of the plurality of graphs in response to an input;
    intersecting, via the marker, the plurality of graphs each representing a measured physiologic parameter versus time at a common point on the time axis; and
    displaying physiologic values at the common point in time of each of the plurality of graphs, continuously and in real-time, as the marker moves across the plurality of graphs.

12. The method according to claim 11, further comprising representing each graph of the measured physiologic parameters as a trend of the measured physiologic parameter over a period of time.

13. The method according to claim 11, further comprising stacking the plurality of graphs with respect to each other in a vertical orientation and in a non-overlapping manner.

14. The method according to claim 13, wherein the marker is a vertical time scroll bar.

15. The method according to claim 11, further comprising moving the marker to a previous measured time period or point in time corresponding to historical medical events of interest for evaluating the measured physiologic parameters during that measured time period or point in time.

16. A non-transitory computer-readable storage medium encoded with a program that, when executed by a processor, causes the processor to:
    collect measured physiologic parameters via at least one sensor;
    store the measured physiologic parameters within a storage unit of a monitor in operable communication with the at least one sensor;
    generate a plurality of graphs each representing the measured physiologic parameters versus time, the plurality of graphs configured to be aligned with respect to each other along a time axis;
    move a marker along the time axis of each of the plurality of graphs in response to an input;
    intersect, via the marker, the plurality of graphs each representing a measured physiologic parameter versus time at a common point on the time axis; and
    display physiologic values at the common point in time of each of the plurality of graphs, continuously and in real-time, as the marker moves across the plurality of graphs.

17. The non-transitory computer-readable storage medium of claim 16, wherein the processor is further caused to stack the plurality of graphs with respect to each other in a vertical orientation and in a non-overlapping manner.

18. The non-transitory computer-readable storage medium of claim 16, wherein the processor is further caused to move the marker across one graph of the plurality of graphs to a point in time, such that all the measured physiologic parameters of all of the plurality of graphs displayed on the monitor at that point in time are configured to be simultaneously analyzed.

* * * * *